United States Patent
Chu et al.

(10) Patent No.: US 11,406,342 B2
(45) Date of Patent: Aug. 9, 2022

(54) DEVICE AND METHOD FOR POST-PROCESSING OF COMPUTED TOMOGRAPHY

(71) Applicant: Wistron Corporation, New Taipei (TW)

(72) Inventors: Che-Wei Chu, New Taipei (TW); Chun-Peng Hsu, New Taipei (TW)

(73) Assignee: Wistron Corporation, New Taipei (TW)

( * ) Notice: Subject to any disclaimer, the term of this patent is extended or adjusted under 35 U.S.C. 154(b) by 38 days.

(21) Appl. No.: 16/809,505

(22) Filed: Mar. 4, 2020

(65) Prior Publication Data

US 2021/0219936 A1    Jul. 22, 2021

(30) Foreign Application Priority Data

Jan. 20, 2020    (TW) .................................. 109101870

(51) Int. Cl.
*A61B 6/00* (2006.01)
*G06T 7/12* (2017.01)
*G06T 7/00* (2017.01)

(52) U.S. Cl.
CPC .......... *A61B 6/5241* (2013.01); *G06T 7/0012* (2013.01); *G06T 7/12* (2017.01); *G06T 2207/10081* (2013.01)

(58) Field of Classification Search
CPC ..... A61B 6/032; A61B 6/5241; A61B 6/5217; G06T 7/11; G06T 7/12; G06T 7/0012; G16H 30/40
See application file for complete search history.

(56) References Cited

U.S. PATENT DOCUMENTS

| | | | | |
|---|---|---|---|---|
| 6,138,045 A | * | 10/2000 | Kupinski | G06T 7/0012 378/37 |
| 2009/0226057 A1 | * | 9/2009 | Mashiach | G06T 5/002 382/128 |

(Continued)

OTHER PUBLICATIONS

P. Márquez-Neila, L. Baumela and L. Alvarez, "A Morphological Approach to Curvature-Based Evolution of Curves and Surfaces," in IEEE Transactions on Pattern Analysis and Machine Intelligence, vol. 36, No. 1, pp. 2-17, Jan. 2014, doi: 10.1109/TPAMI.2013.106. (Year: 2014).*

(Continued)

*Primary Examiner* — Vu Le
*Assistant Examiner* — Julius Chai
(74) *Attorney, Agent, or Firm* — JCIPRNET

(57) ABSTRACT

A device and a method for post-processing of computed tomography (CT), which are adapted to improve an identification image of a focal nodular hyperplasia (FNH) of a liver, are provided. The method includes: obtaining the identification image including a liver region and a non-liver region and a Hounsfield unit (HU) value of each pixel corresponding the identification image, wherein the liver region includes an FNH candidate region; calculating an average HU of the liver region; adjusting an HU value of the non-liver region to the average HU value of the liver region with respect to the identification image to generate a processed identification image; and updating the FNH candidate region according to a morphological algorithm based on the processed identification image to generate an updated FNH candidate region.

10 Claims, 5 Drawing Sheets

(56) References Cited

U.S. PATENT DOCUMENTS

| | | | |
|---|---|---|---|
| 2013/0322710 A1* | 12/2013 | Notte | G06T 7/11 |
| | | | 382/128 |
| 2014/0037170 A1* | 2/2014 | Sekiguchi | G06T 7/0012 |
| | | | 382/131 |
| 2014/0044328 A1* | 2/2014 | Matsuda | G06T 7/0012 |
| | | | 382/128 |
| 2015/0030219 A1* | 1/2015 | Madabhushi | G06T 7/149 |
| | | | 382/128 |
| 2017/0270664 A1* | 9/2017 | Hoogi | A61B 6/5217 |
| 2018/0247414 A1* | 8/2018 | Novikov | G06K 9/6276 |
| 2021/0065877 A1* | 3/2021 | Chen | G06T 7/11 |

OTHER PUBLICATIONS

22. T. F. Chan and L. A. Vese, "Active contours without edges," in IEEE Transactions on Image Processing, vol. 10, No. 2, pp. 266-277, Feb. 2001, doi: 10.1109/83.902291. (Year: 2001).*

23. T. Chan and Wei Zhu, "Level set based shape prior segmentation," 2005 IEEE Computer Society Conference on Computer Vision and Pattern Recognition (CVPR'05), 2005, pp. 1164-1170 vol. 2, doi: 10.1109/CVPR.2005.212. (Year: 2005).*

Li et al. "Distance Regularized Level Set Evolution and Its Application to Image Segmentation", IEEE Transactions on Image Processing vol. 19, No. 12, Dec. 2010 (Year: 2010).*

Khare et al. "Medical Image Segmentation using Level set Method without reinitialization", International Conference on Signal, Image and Video Processing, 2012. (Year: 2012).*

Oliveira et al. "Segmentation of liver, its vessels and lesions from CT images for surgical planning", BioMedical Engineering OnLine, 2011. (Year: 2011).*

Vanmore et al. "Survey on Automatic Liver Segmentation Techniques from Abdominal CT Images", Proceedings of the International Conference on Intelligent Computing and Control Systems, 2019. (Year: 2019).*

* cited by examiner

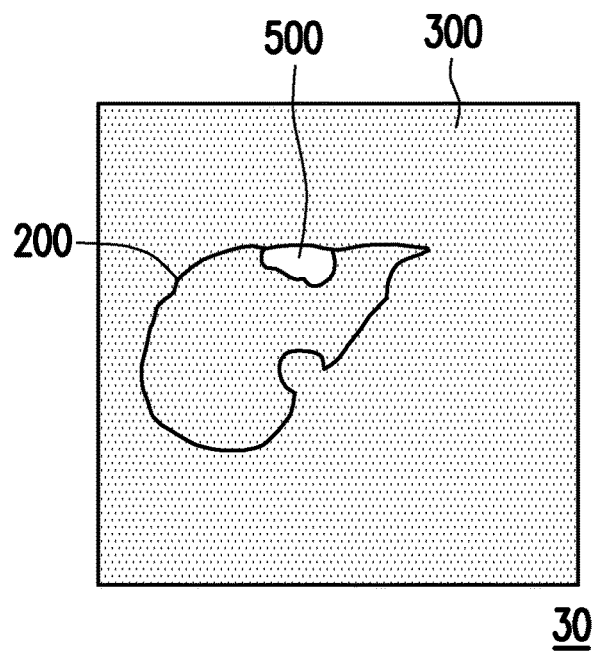

FIG. 4C

| Obtaining the identification image regarding to a liver contour and a non-liver contour and an HU value of each pixel corresponding to the identification image, wherein the liver contour comprises an FNH candidate contour | ~S501 |

↓

| Adjusting an HU value of the non-liver contour to an average HU value of the liver contour in respect with the identification image to generate a processed identification image | ~S502 |

↓

| Updating the FNH candidate contour according to a morphological algorithm based on the processed identification image to generate an updated FNH candidate contour | ~S503 |

FIG. 5

DEVICE AND METHOD FOR POST-PROCESSING OF COMPUTED TOMOGRAPHY

CROSS-REFERENCE TO RELATED APPLICATION

This application claims the priority benefit of Taiwan application serial no. 109101870, filed on Jan. 20, 2020. The entirety of the above-mentioned patent application is hereby incorporated by reference herein and made a part of this specification.

TECHNICAL FIELD

The invention relates to a device and a method, and more particularly, relates to a device and method for post-processing of computed tomography.

BACKGROUND

With the gradual popularization of deep learning, as more medical institutions are beginning to accept and look forward to use computer science for help radiologists in determining computed tomography (CT) images of patients, there are also more teams investing in development of a liver tumor identification system. Most of the current computer science and technology focuses on the identification of malignant hepatocellular carcinoma (HCC), but fails to focus on image identification of benign tumors such as hemangioma or focal nodular hyperplasia (FNH). However, for livers with several conditions, it is clearly not enough to only determining malignancies. Therefore, finding a way to determine the benign tumor of the liver to assist doctors in determining the liver condition of the patient is one of the goals of those skilled in the art.

SUMMARY

The invention provides a device and a method for post-processing of computed tomography which can improve an FNH identification image of so an FNH identification result may be closer to an actual FNH boundary and false positives of the FNH identification result may be reduced.

A device for post-processing of computed tomography of the invention is adapted to improve an identification image of a focal nodular hyperplasia (FNH) of a liver, wherein the device includes a processor, a storage medium and a transceiver. The storage medium stores a plurality of modules. The processor is coupled to the storage medium and the transceiver, and accesses and executes a plurality of modules, wherein the module include a data collection module and a computing module. The data collection module obtains the identification image regarding to a liver region and a non-liver region and a Hounsfield unit(HU) value of each pixel corresponding to the identification image through the transceiver, wherein the liver region includes an FNH candidate region. The computing module adjusts an HU value of the non-liver region to an average HU value of the liver region in respect with the identification image to generate a processed identification image, and updates the FNH candidate region according to a morphological algorithm based on the processed identification image to generate an updated FNH candidate region.

In an embodiment of the invention, the computing module determines that the updated FNH candidate region represents a correct identification result of the FNH in response to an intersection set of the updated FNH candidate region and the FNH candidate region exceeding a threshold.

In an embodiment of the invention, the computing module determines that the updated FNH candidate region represents an incorrect identification result of the FNH in response to an intersection set of the updated FNH candidate region and the FNH candidate region not exceeding a threshold.

In an embodiment of the invention, the threshold is associated with a union set of the updated FNH candidate region and the FNH candidate region.

In an embodiment of the invention, the morphological algorithm is an active contours without edges (ACWE) method.

A method for post-processing of computed tomography of the invention is adapted to improve an identification image of a focal nodular hyperplasia (FNH) of a liver. The method includes: obtaining the identification image regarding to a liver region and a non-liver region and an HU value of each pixel corresponding to the identification image, wherein the liver region includes an FNH candidate region; adjusting an HU value of the non-liver region to the average HU value of the liver region in respect with the identification image to generate a processed identification image; and updating the FNH candidate region according to a morphological algorithm based on the processed identification image to generate an updated FNH candidate region.

In an embodiment of the disclosure, the method further includes: determining that the updated FNH candidate region represents an identification result of the FNH in response to an intersection set of the updated FNH candidate region and the FNH candidate region exceeding a threshold.

In an embodiment of the disclosure, the method further includes: determining that the updated FNH candidate region represents an incorrect identification result in response to an intersection set of the updated FNH candidate region and the FNH candidate region not exceeding a threshold.

In an embodiment of the invention, the threshold is associated with a union set of the updated FNH candidate region and the FNH candidate region.

In an embodiment of the invention, the morphological algorithm is an active contours without edges (ACWE) method.

Based on the above, the device and method for post-processing of computed tomography of the invention can significantly improve the accuracy of the FNH identification. As a result, doctors will be able to more accurately determine information such as the size and location of the FNH.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 4C is a schematic diagram illustrating a processed identification image in which the incorrect updated FNH candidate region and the FNH candidate region are eliminated according an embodiment of the invention.

FIG. 5 is a flowchart illustrating a method for post-processing of CT according an embodiment of the invention.

DESCRIPTION OF THE EMBODIMENTS

Figure 1:
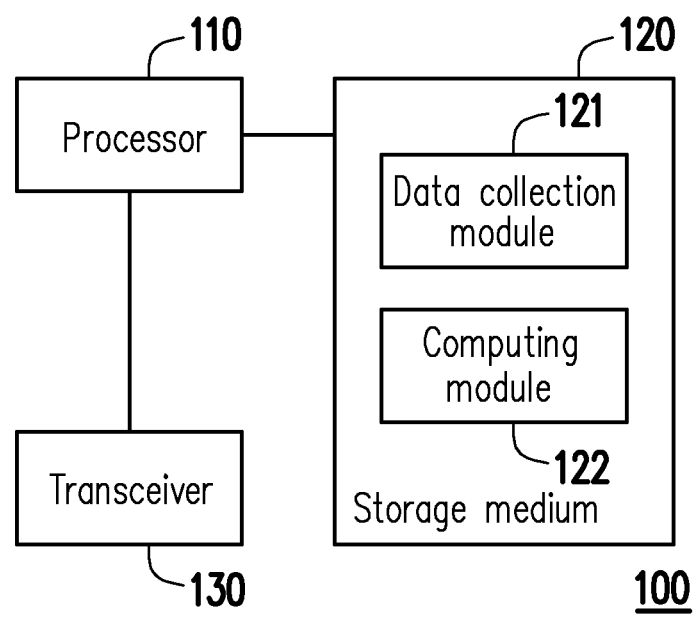
FIG. 1 is a schematic diagram illustrating a device for post-processing of CT according an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

FIG. 1 is a schematic diagram illustrating a device 100 for post-processing of CT according an embodiment of the invention. The device 100 is adapted to improve an identification image of a focal nodular hyperplasia (FNH) of a liver. The device 100 may include a processor 110, a storage medium 120 and a transceiver 130.

The processor 110 is, for example, a central processing unit (CPU) or other programmable micro control units (MCU) for general purpose or special purpose, a microprocessor, a digital signal processor (DSP), a programmable controller, an application specific integrated circuit (ASIC), a graphics processing unit (GPU), an arithmetic logic unit (ALU), a complex programmable logic device (CPLD), a field programmable gate array (FPGA) or other similar elements or a combination of above-mentioned elements. The processor 110 may be coupled to the storage medium 120 and the transceiver 130, and may access or execute a plurality of modules and various applications stored in the storage medium 120.

The storage medium 120 is, for example, a random access memory (RAM), a read-only memory (ROM), a flash memory, a hard disk drive (HDD), a hard disk drive (HDD), a solid state drive (SSD) or other similar elements in any stationary or movable form, or a combination of the above-mentioned elements, and is used to store the modules and various applications that may be executed by the processor 110. In this embodiment, the storage medium 120 may store the modules including a data collection module 121 and a computing module 122, ad their functions will be described later.

The transceiver 130 transmits and receives signals in a wired or wireless manner. The transceiver 130 can also perform operations such as low noise amplifying, impedance matching, frequency mixing, up and down frequency conversion, filtering, amplification and similar operations.

Figure 2A:
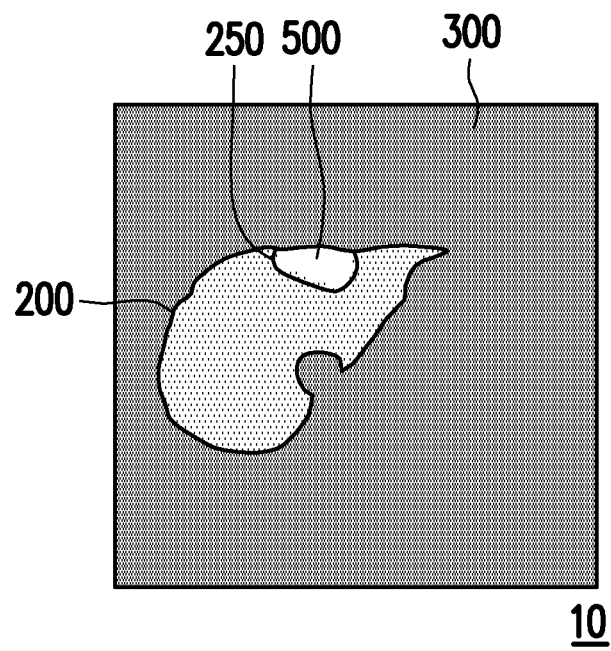
FIG. 2A is a schematic diagram illustrating an identification image of a liver having FNH according an embodiment of the invention.

The data collection module 121 may obtain an identification image of a liver through the transceiver 130. FIG. 2A is a schematic diagram illustrating an identification image 10 of a liver having FNH according an embodiment of the invention. Here, the identification image 10 may include a liver region 200 surrounding the liver parenchyma and a non-liver region 300 surrounding the non-liver parenchyma (i.e., a black portion in FIG. 2A). The identification image 10 may also include an FNH candidate region 250 surrounding an FNH 500. The identification image 10, the liver region 200, the non-liver region 300 or the FNH candidate region 250 are generated by, for example, identifying an original liver CT image based on technologies including artificial intelligence (AI), machine learning algorithm or deep learning algorithm, but the invention is not limited thereto. In addition, the data collection module 121 may further obtain the identification image regarding to the liver and an HU (Hounsfield unit) value of each pixel corresponding to the identification image through the transceiver 130.

In general, the portion surrounded by the FNH candidate region 250 does not completely match the FNH 500, and there may be an error between the two. In order to minimize said error, the computing module 122 may perform a post-processing on the identification image 10.

First, the computing module 122 may calculate an average HU value of the liver parenchyma in the liver region 200 and adjust an HU value of the non-liver parenchyma in the non-liver region 300 to the average HU value of the liver parenchyma, as shown by Equation (1), wherein $P_1$ represents the liver parenchyma (i.e., a set of pixels in the liver region 200); $P_2$ represents the non-liver parenchyma (i.e., a set of pixels in the non-liver region 300); x represents pixels in the identification image 10; $L_0(x)$ represents an unadjusted HU value of x; $L_1(x)$ represents an adjusted HU value of x; $x_i$ represents an i-th pixel in the liver region 200 and n represents a total of pixels in the liver region 200.

$$L_1(x) = \begin{cases} L_0(x), & \text{if } x \in P_1 \\ \frac{1}{n}\sum_{i=1}^{n} L_0(x_i), & \text{if } x \in P_2 \end{cases} \quad (1)$$

Figure 2B:
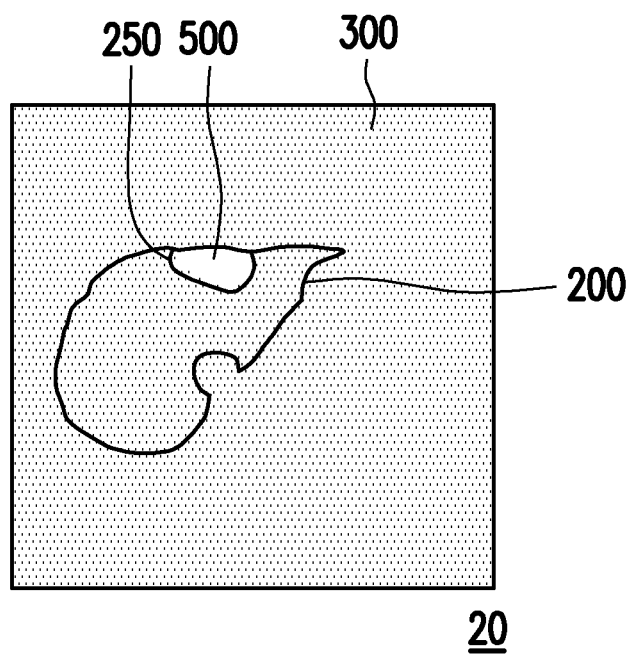
FIG. 2B is a schematic diagram illustrating a processed identification image according an embodiment of the invention.

FIG. 2B is a schematic diagram illustrating a processed identification image 20 according an embodiment of the invention. The computing module 122 may modify pixels in the non-liver region 300 in the identification image 10 based on Equation (1) so that the HU value of the non-liver region 300 is closer to the average HU value of the liver region 200. In this way, a contrast between the non-liver parenchyma in the non-liver region 300 and the liver parenchyma in the liver region 200 may be reduced so that a contrast between the FNH 500 in the FNH candidate region 250 and the liver parenchyma in the liver region 200 becomes clearer.

Figure 3:
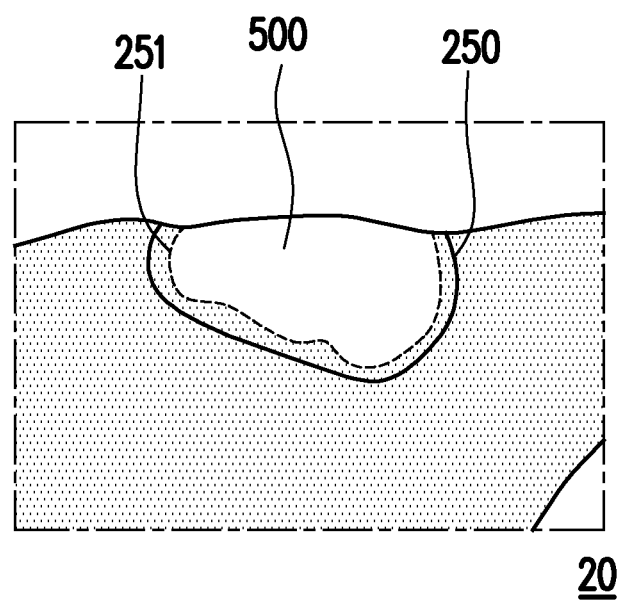
FIG. 3 is a schematic diagram illustrating an updated FNH candidate region according to an embodiment of the invention.

Next, the computing module 122 may update the FNH candidate region 250 according to a morphological algorithm based on the processed identification image 20 to generate an updated FNH candidate region 251, as shown by FIG. 3. FIG. 3 is a schematic diagram illustrating the updated FNH candidate region 251 according to an embodiment of the invention. The morphological algorithm described above is, for example, an active contours without edges (ACWE) method. First, the computing module 122 may create a regular expression of an ACWE model as shown by Equation (2), wherein F represents an energy function of the ACWE model; μ or υ represents a parameter greater than or equal to 0 (in this embodiment, υ=0); C represents a curve of a region boundary; length(C) is a length of C; inside(C) represents pixels inside the curve of the region boundary; $c_1$ represents a pixel average value of inside(C); outside(C) represents pixels outside the curve of the region boundary; $c_2$ represents a pixel average value of outside(C); $\lambda_1$ or $\lambda_2$ represents a parameter greater than 0 and I(x) represents a pixel value of the pixel x.

$$F(c_1,c_2,C)=\mu\cdot\text{length}(C)+\upsilon\cdot\text{area}(\text{inside}(C))+\lambda_1\int_{\text{inside}(C)}\|I(x)-c_1\|dx+\lambda_2\int_{\text{outside}(C)}\|I(x)-c_2\|dx \quad (2)$$

Then, the computing module 122 may find a minimum value of the energy function F through iteration to solve for $\lambda_1$ and $\lambda_2$, thereby calculating a boundary closest to the FNH 500. The computing module 122 may use, for example, a level set method to track the boundary of the FNH 500, as shown by Equation (3), wherein) $u^j(x)$ is a level set function of the pixel x after a j-th step is performed; $D_d$ represents an expansion; $E_d$ represents an erosion; $\nabla$ represents a gradient and $SI_d \circ IS_d$ represents a combination of the expansion and the erosion (i.e., performing $IS_d$ first (i.e., expanding before eroding to passivate for recesses) before performing $SI_d$ (eroding before expanding to passivate for protrusion), $\lambda_1$ or $\lambda_2$ is a parameter greater than 0; $\mu$ is a parameter greater than or equal to 0 and I(x) is a pixel value of the pixel x. After $u^2(x)$ is calculated, the computing module 122 may determine the boundary closest to the FNH 500 (i.e., the updated FNH candidate region 251) based on $u^2(x)$.

$$\begin{cases} u^1(x) = \begin{cases} 1, \text{ if } |\nabla u^0|(\lambda_1(I-c_1)^2 - \lambda_2(I-c_2)^2)(x) < 0 \\ 0, \text{ if } |\nabla u^0|(\lambda_1(I-c_1)^2 - \lambda_2(I-c_2)^2)(x) > 0 \\ u^0(x), \text{ otherwise} \end{cases} \\ u^2(x) = ((SI_d \circ IS_d)^\mu u^1)(x) \end{cases} \quad (3)$$

Figure 4A:
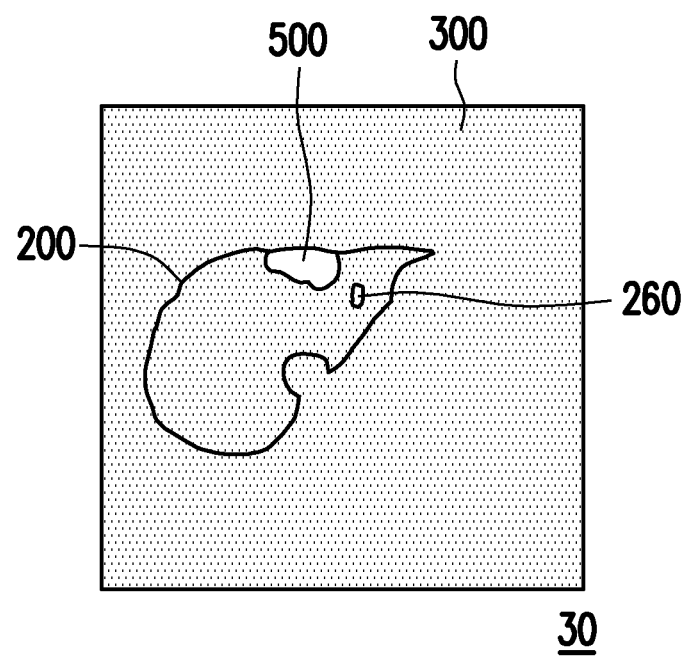
FIG. 4A is a schematic diagram illustrating a processed identification image containing an incorrect FNH candidate region according an embodiment of the invention.
Figure 4B:
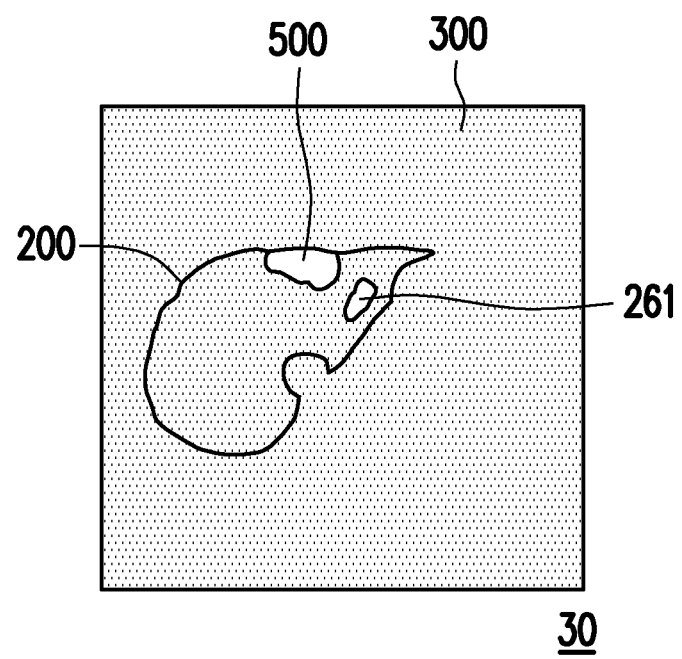
FIG. 4B is a schematic diagram illustrating the updated identification image based on the incorrect FNH candidate region according an embodiment of the invention.

It should be noted that, an initial point of the ACWE method is selected from the FNH candidate region predicted by AI. If AI determines the normal liver parenchyma incorrectly as the FNH, the computing module 122 may expand the updated FNH candidate region into a region including the entire liver parenchyma according to the incorrect initial point. FIG. 4A is a schematic diagram illustrating a processed identification image 30 containing an incorrect FNH candidate region 260 according an embodiment of the invention. FIG. 4B is a schematic diagram illustrating the updated identification image 261 based on the incorrect FNH candidate region 260 according an embodiment of the invention. Referring to FIG. 4A and FIG. 4B together, it is assumed that AI determines a region of the normal liver parenchyma incorrectly as the incorrect FNH candidate region 260, the computing module 122 may generate an incorrect updated FNH candidate region 261 according to the incorrect FNH candidate region 260 based on the ACWE method. After multiple iterative calculations, the incorrect updated FNH candidate region 261 may be expanded to include a region including the entire normal liver parenchyma.

To avoid generating the incorrect updated FNH candidate region, the computing module 122 may determine that the updated FNH candidate region represents a correct FNH identification result in response to an intersection set of the updated FNH candidate region and the FNH candidate region exceeding a threshold, and determine that the updated FNH candidate region represents an incorrect FNH identification result in response to the intersection set of the updated FNH candidate region and the FNH candidate region not exceeding the threshold. Here, the threshold is associated with a union set of the updated FNH candidate region and the FNH candidate region, as shown by Equation (4) wherein $Y_{AI}$ represents the FNH candidate region predicted by AI; $Y_p$ represents the updated FNH candidate region calculated by the computing module 122 based on the ACWE method; T represents a constant, R=1 means that the FNH identification result is correct and R=0 means that the FNH identification result is incorrect.

$$R = \begin{cases} 1, \text{ if } Y_{AI} \cap Y_P > T \cdot Y_{AI} \cup Y_P \\ 0, \text{ if } Y_{AI} \cap Y_P \leq T \cdot Y_{AI} \cup Y_P \end{cases}, \forall Y_{AI} = 1 \quad (4)$$

For instance, the computing module 122 may determine that the updated FNH candidate region 251 represents a correct identification result of the FNH 500 in response to an intersection set of the updated FNH candidate region 251 and the FNH candidate region 250 exceeding a threshold, as shown by FIG. 3. As another example, the computing module 122 may determine that the updated FNH candidate region 261 represents an incorrect identification result of the FNH 500 in response to the intersection set of the updated FNH candidate region 261 and the FNH candidate region 260 not exceeding the threshold, as shown by FIG. 4B. In order to reduce false positives of the identification result of the FNH 500, the computing module 122 may eliminate the updated FNH candidate region 261 (and/or the FNH candidate region 260), as shown by FIG. 4C. FIG. 4C is a schematic diagram illustrating the processed identification image 30 in which the incorrect updated FNH candidate region 261 and the FNH candidate region 260 are eliminated according an embodiment of the invention.

FIG. 5 is a flowchart illustrating a method for post-processing of CT according an embodiment of the invention, wherein the method may be implemented by the device 100 shown by FIG. 1. In step S501, the identification image regarding to a liver region and a non-liver region and an HU value of each pixel corresponding to the identification image are obtained, wherein the liver region includes an FNH candidate region. In step S502, an HU value of the non-liver region is adjusted to the average HU value of the liver region in respect with the identification image to generate a processed identification image. In step S503, the FNH candidate region is updated according to a morphological algorithm based on the processed identification image to generate an updated FNH candidate region.

In summary, the device and method for post-processing of computed tomography of the invention can significantly improve the accuracy of the FNH identification. The invention may regulate the non-liver region in the identification image so that the HU value of the non-liver region is equivalent to the average HU value of the liver region. In this way, the difference between the HU value of the FNH and the HU value of normal parts of the liver will become clearer so that the FNH identification also becomes easier. In addition, the morphological algorithm is used to update the FNH candidate region to make the boundary of the updated FNH candidate region closer to the real FNH through operations such as expansion or erosion. Based on the updated FNH candidate profile, doctors will be able to more accurately determine the size and location of the FNH. On the other hand, the invention may also determine whether the updated FNH candidate region corresponds to the correct determination result according to the intersection set or the union set of the updated FNH candidate region and the original FNH candidate region, so as to prevent the normal parts of the liver from being determined as the FNH to reduce false positives of the identification result.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A device for post-processing of computed tomography, adapted to improve an identification image of a focal nodular hyperplasia (FNH) of a liver, wherein the device comprises:
a transceiver;
a storage medium, storing a plurality of modules; and
a processor, coupled to the storage medium and the transceiver, and accessing and executing a plurality of modules, wherein the modules comprises:
a data collection module, configured to obtain the identification image containing a liver region and a non-liver region, and a Hounsfield unit (HU) value of each pixel corresponding to the identification image through the transceiver, wherein the liver region comprises an FNH candidate region; and
a computing module, configured to adjust an HU value of the non-liver region to an average HU value of the liver region with respect to the identification image to generate a processed identification image, and updating the FNH candidate region according to a morphological algorithm based on the processed identification image to generate an updated FNH candidate region, wherein an initial point of the morphological algorithm is selected from the FNH candidate region predicted by artificial intelligence (AI),
wherein the computing module is further configured to track a boundary of the FNH candidate region by calculating a level set function, and determine the boundary of the FNH candidate region based on the level set function to generate the updated FNH candidate region,
wherein the level set function comprising a combination of an expansion and an erosion,
wherein the morphological algorithm comprising an energy function which is expressed as the following equation $F(c_1, c_2, C) = \mu \cdot \text{length}(C) + v \cdot \text{area}(\text{inside}(C)) + \lambda_1 \int_{\text{inside}(C)} \|I(x) - c_1\| dx + \lambda_2 \int_{\text{outside}(C)} \|I(x) - c_2\| dx$ wherein F represents the energy function, C represents a curve of a region boundary; length(C) is a length of C, inside(C) represents pixels inside the curve of the region boundary; $c_1$ represents a pixel average value of inside(C); outside(C) represents pixels outside the curve of the region boundary; $c_2$ represents a pixel average value of outside(C); $\mu$, $v$, $\lambda_1$ and $\lambda_2$ represent parameters, and I(x) represents a pixel value of the pixel x.

2. The device according to claim 1, wherein the computing module determines that the updated FNH candidate region represents a correct identification result of the FNH in response to an intersection set of the updated FNH candidate region and the FNH candidate region exceeding a threshold.

3. The device according to claim 1, wherein the computing module determines that the updated FNH candidate region represents an incorrect identification result of the FNH in response to an intersection set of the updated FNH candidate region and the FNH candidate region not exceeding a threshold.

4. The device according to claim 2, wherein the threshold is associated with a union set of the updated FNH candidate region and the FNH candidate region.

5. The device according to claim 1, wherein the morphological algorithm is an active contours without edges (ACWE) method.

6. A method for post-processing of computed tomography, adapted to improve an identification image of a focal nodular hyperplasia (FNH) of a liver, wherein the method comprises:
obtaining the identification image containing a liver region and a non-liver region and an HU value of each pixel corresponding to the identification image, wherein the liver region comprises an FNH candidate region;
adjusting an HU value of the non-liver region to an average HU value of the liver region with respect to the identification image to generate a processed identification image;
updating the FNH candidate region according to a morphological algorithm based on the processed identification image to generate an updated FNH candidate region, wherein an initial point of the morphological algorithm is selected from the FNH candidate region predicted by artificial intelligence (AI); and
tracking a boundary of the FNH candidate region by calculating a level set function, and determine the boundary of the FNH candidate region based on the level set function to generate the updated FNH candidate region,
wherein the level set function comprising a combination of an expansion and an erosion,
wherein the morphological algorithm comprising an energy function which is expressed as the following equation:

$F(c_1, c_2, C) = \mu \cdot \text{length}(C) + v \cdot \text{area}(\text{inside}(C)) + \lambda_1 \int_{\text{inside}(C)} \|I(x) - c_1\| dx + \lambda_2 \int_{\text{outside}(C)} \|I(x) - c_2\| dx$ wherein F represents the energy function, C represents a curve of a region boundary; length(C) is a length of C, inside(C) represents pixels inside the curve of the region boundary; $c_1$ represents a pixel average value of inside(C); outside(C) represents pixels outside the curve of the region boundary; $c_2$ represents a pixel average value of outside(C); $\mu$, $v$, $\lambda_1$ and $\lambda_2$ represent parameters, and I(x) represents a pixel value of the pixel x.

7. The method according to claim 6, further comprising:
determining that the updated FNH candidate region represents an identification result of the FNH in response to an intersection set of the updated FNH candidate region and the FNH candidate region exceeding a threshold.

8. The method according to claim 6, further comprising:
determining that the updated FNH candidate region represents an incorrect identification result in response to an intersection set of the updated FNH candidate region and the FNH candidate region not exceeding a threshold.

9. The method according to claim 7, wherein the threshold is associated with a union set of the updated FNH candidate region and the FNH candidate region.

10. The method according to claim 6, wherein the morphological algorithm is an active contours without edges (ACWE) method.

* * * * *